US009658167B2

(12) United States Patent
Forster et al.

(10) Patent No.: US 9,658,167 B2
(45) Date of Patent: May 23, 2017

(54) SENSOR LABELS THAT LOG EVENTS AGAINST TIME

(71) Applicant: Avery Dennison Retail Information Services, LLC, Mentor, OH (US)

(72) Inventors: Ian James Forster, Essex (GB); Sjoerd J. Van Driesten, Bodegraven (NL)

(73) Assignee: AVERY DENNISON RETAIL INFORMATION SERVICES, LLC, Westborough, MA (US)

( * ) Notice: Subject to any disclaimer, the term of this patent is extended or adjusted under 35 U.S.C. 154(b) by 57 days.

(21) Appl. No.: 14/568,602

(22) Filed: Dec. 12, 2014

(65) Prior Publication Data
US 2016/0169811 A1    Jun. 16, 2016

(51) Int. Cl.
*G01N 21/78* (2006.01)
*G01D 9/00* (2006.01)
(Continued)

(52) U.S. Cl.
CPC ............. *G01N 21/78* (2013.01); *G01D 9/005* (2013.01); *G01K 11/12* (2013.01); *G01N 31/22* (2013.01); *G01N 33/53* (2013.01); *A61B 5/06* (2013.01); *B01L 2200/12* (2013.01); *B01L 2300/0816* (2013.01); *G01N 21/6428* (2013.01); *G01N 21/783* (2013.01); *G01N 21/80* (2013.01); *G01N 21/81* (2013.01); *G01N 21/8483* (2013.01); *G01N 31/00* (2013.01); *G01N 31/223* (2013.01); *G01N 33/50* (2013.01); *G01N 33/531* (2013.01); *G01N 33/5304* (2013.01); *G01N 2021/6439* (2013.01); *G01N 2203/0051* (2013.01)

(58) Field of Classification Search
CPC ...... G01N 33/531; G01N 33/50; G01N 33/53; G01N 31/223; G01N 31/22; G01N 31/00; G01N 21/78; G01N 21/8483; G01N 21/6428; A61B 5/06; B01L 2200/12; B01L 2300/0816; B01N 2021/6439
See application file for complete search history.

(56) References Cited

U.S. PATENT DOCUMENTS 7,244,500 B2 * 7/2007 Watts ........................ G02F 1/15
428/408
2002/0168692 A1 * 11/2002 Cass .................. G01N 33/6803
435/7.9

(Continued)

*Primary Examiner* — Jennifer Wecker
(74) *Attorney, Agent, or Firm* — Avery Dennison Retail Information Services, LLC

(57) ABSTRACT

Disposable or single-use sensor labels sense a parameter and record the sensed parameter having: a semi-permeable medium or substrate with a parameter-sensitive and activatable developer. The developer, when activated, exhibits a detectable manifestation of a changed state that progresses over time. The detectable manifestation of this changed state is read and recorded to log parameter change data. Further, a method of using the sensor label monitors viability of a material associated with the label, such as for freshness and security assessment that is recorded for archival or reporting or quality control purposes. A changed state is exhibited that progresses over time, associating the label with a material to be monitored and positioning same into a given environment, and the recording can track the changed state against time.

16 Claims, 1 Drawing Sheet

(51) Int. Cl.
*G01N 27/00* (2006.01)
*G01N 33/53* (2006.01)
*G01N 31/22* (2006.01)
*G01K 11/12* (2006.01)
*G01N 33/531* (2006.01)
*G01N 33/68* (2006.01)
*G01N 21/84* (2006.01)
*A61B 5/06* (2006.01)
*G01N 21/64* (2006.01)
*G01N 33/50* (2006.01)
*G01N 31/00* (2006.01)
*G01N 21/80* (2006.01)
*G01N 21/81* (2006.01)

(56) References Cited

U.S. PATENT DOCUMENTS

| | | | | |
|---|---|---|---|---|
| 2003/0068657 A1* | 4/2003 | Lin | B01L 3/5085 | 506/9 |
| 2008/0118398 A1* | 5/2008 | Birch | G01N 33/5438 | 422/63 |
| 2012/0135527 A1* | 5/2012 | Bangera | G08B 21/245 | 436/3 |
| 2012/0244623 A1* | 9/2012 | Patel | G09F 3/0292 | 436/2 |
| 2013/0210048 A1* | 8/2013 | Chandrapati | C12Q 1/04 | 435/18 |
| 2014/0001058 A1* | 1/2014 | Ghaffari | G01N 27/327 | 205/792 |

* cited by examiner

SENSOR LABELS THAT LOG EVENTS AGAINST TIME

BACKGROUND

Field of the Disclosure

The present subject matter relates to labels that exhibit sensor properties that change when exposed to a stimulus in order to manifest environmental conditions that are sensed by the label, thereby indicating a change in a material such as an article of commerce with which the label is associated.

Description of Related Art

Labels having the ability to be responsive to environmental changes to which the labels are exposed are known. Some such labels are battery powered electronic devices with electric switching and that are relatively expensive and not intended to be disposable, at times designed for multiple uses. Others provide a time indicator by selecting a liquid indicator with a given viscosity that determined the rate of migration of the liquid. Other sensor-type labels include Avery® TTSensor™ labels that have the ability to display an integrated result and/or are sensor active labels. Some of the prior labels are of a two-piece design, having an indicator label and an activator label, and monitoring begins when the activator label is applied to the article of commerce or other material, typically over the indictor label. Visual indicators are typically part of these types of prior systems, such a color changes in response to predetermined exposure conditions such as temperature. Variations include anti-microbial air release active labels, useful for monitoring the integrity of cold-chain perishable materials, such as food; fungicidal packaging to address susceptibility to degradation from moisture exposure; and air or steam release systems incorporating one-way valves.

SUMMARY

There are several aspects or embodiments of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as may be set forth in the claims appended hereto.

In one embodiment, a disposable or single-use label senses a parameter and records the sensed parameter, comprising: a semi-permeable medium and a parameter-sensitive and activatable developer on the semi-permeable medium. When activated, the developer exhibits a detectable manifestation of a changed state that progresses over time. A reader captures the detectable manifestation of this changed state, and a recorder of the detectable manifestation of this changed state logs parameter change data. In an alternate embodiment, the reader notes the time of the reading, and the recorder logs parameter change data against time.

In another embodiment, a disposable or single-use label senses a parameter and records the sensed parameter, comprising: a semi-permeable medium having a parameter-sensitive and activatable developer that includes a reactive chemical within a solvent. Typically when activated, the solvent carries the reactive chemical through at least one layer of the semi-permeable membrane, whereupon the developer exhibits a detectable manifestation of a changed state that progresses over time. A reader captures the detectable manifestation of this changed state, and a recorder of the detectable manifestation of this changed state logs parameter change data. In an alternate embodiment, the reader notes the time of the reading, and the recorder logs parameter change data against time.

In an additional embodiment, a disposable or single-use label senses a parameter and records the sensed parameter, comprising: a semi-permeable medium having a parameter-sensitive and activatable developer. When activated, the developer exhibits a detectable manifestation of a changed state that progresses over time, which detectable manifestation is recognized by an RFID chip on the label, thereby capturing the detectable manifestation of this changed state, and a recorder receives data from the RFID chip and the detectable manifestation of this changed state is logged. In an alternate embodiment, the RFID chip notes the time of the reading, and the recorder logs parameter change data against time. Typically the recorder is remote from the RFID chip.

In a further embodiment, a disposable or single-use label senses a parameter and records the sensed parameter, comprising: a semi-permeable medium having a parameter-sensitive and activatable developer. When activated, the developer exhibits an optically detectable manifestation of a changed state that progresses over time, which detectable manifestation is recognized by an optical detector which can be on the label, thereby capturing the detectable manifestation of this changed state, and a recorder receives data from the optical detector and the detectable manifestation of this changed state is logged. In an alternate embodiment, the time of the optical reading is captured, and the recorder logs parameter change data against time.

In an added embodiment, a sensor label that is designed for and fabricated to be for a single use and disposable is secured to an article of commerce and senses a parameter and records the sensed parameter. The sensor label includes: a semi-permeable medium and a parameter-sensitive and activatable developer on the semi-permeable medium. When activated, the developer exhibits a detectable diffusion change with respect to the semi-permeable membrane and that progresses over time. A reader captures the diffusion change, and a recorder of the detectable manifestation of this changed state logs parameter change data. In an alternate embodiment, the reader notes the time of the reading, and the recorder logs parameter change data against time.

In an embodiment, a disposable or single-use label senses a parameter and records the sensed parameter, comprising: a semi-permeable medium and a parameter-sensitive and activatable developer on the semi-permeable medium. When activated by changes in or threshold achievement with respect to temperature, pressure, pH, moisture, shock, light, UV light, gas development and/or chemical change, and combinations thereof, the developer exhibits a detectable manifestation of a changed state that progresses over time. A reader captures the detectable manifestation of this changed state, and a recorder of the detectable manifestation of this changed state logs parameter change data. In an alternate embodiment, the reader notes the time of the reading, and the recorder logs parameter change data against time.

In a further embodiment, a disposable or single-use label senses a parameter and records the sensed parameter, comprising: a semi-permeable medium and a parameter-sensitive and activatable developer on the semi-permeable medium. The developer is selected from, for example, a thermochromic ink, a piezo-electric layer, a light-sensitive component, an enzyme layer, a micro-encapsulated reagent layer, and combinations thereof. When activated, the developer exhibits a detectable manifestation of a changed state that progresses over time. A reader captures the detectable manifestation of this changed state, and a recorder of the detectable manifestation of this changed state logs parameter change data. In an alternate embodiment, the reader notes the time of the reading, and the recorder logs parameter change data against time.

An embodiment concerns a method of using a label for monitoring viability of a material associated with the label. The method includes providing a label that is fabricated as and intended to be for a single use and/or disposable, the label including a semi-permeable medium having a parameter-sensitive and activatable developer, the developer, when activated, exhibits a changed state that progresses over time. The method includes associating the label with a material to be monitored and positioning same into a given environment, reading the detectable manifestation of this changed state, and recording the detectable manifestation of this changed state in order to log parameter change data. In an embodiment, the method notes the time of the reading and logs parameter change data against time.

A further embodiment concerns a method of using a label for monitoring viability of a material associated with the label. The method includes providing a label that is fabricated as and intended to be for a single use and/or disposable, the label including a semi-permeable medium having a parameter-sensitive and activatable developer, the developer, when activated, exhibits a changed state that progresses over time. The method includes associating the label with a material to be monitored and positioning same into a given environment, using RFID techniques and/or optical reading techniques in order to read the detectable manifestation of this changed state, and recording the detectable manifestation of this changed state in order to log parameter change data. In an embodiment, the method notes the time of the reading and logs parameter change data against time.

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which.

DESCRIPTION OF THE ILLUSTRATED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

The term label as used herein encompasses any variety of sheet-like members that are part of or attached to materials such as articles of commerce in order to convey information associated with the material with which it is associated. These can take the form of shaped sheets or devices, adhesive-backed labels, tags, hang tags, and others known in the art. These often meet the connotation typically associated with a label, namely an area that is intended to direct attention to itself. They will vary according to needs of the particular item, material and/or article with which it is associated or to be associated, exhibiting details that will vary according to specific indicia of the particular item, material or article. Examples of fields of use for these sensor labels are in the food, pharmaceutical and shipping industries.

The present disclosure is especially suitable for label structures designed to record a sensor state against time using a progressive spatial chemical reaction and methods of reading the information such as in an optical or electronic manner. Typically, these sensor labels have the capability and structure to log events against time. These can be considered to be in the category of "smart" sensor labels in that they can provide a record of a sensed parameter or of sensed parameters, including temperature, pressure, shock, pH, moisture, light, UV light, gas presence, gas makeup, combinations thereof and so forth. In particular embodiments, the sensed parameters are captured against time.

An aspect of some embodiments of this disclosure is the reliance on the progress of a solvent carrying a reactive chemical through a layer of semi-permeable medium, for example a layer of paper, in the nature of a developer which "fixes" a change, somewhat in the nature of chromatography. The disclosure labels are considered as simple structures that are nevertheless capable of recording a parameter against time. A display can be generated which is in the form of an optical signal, an electrical signal and/or a characteristic that can be read via RFID technology.

Figure 1:
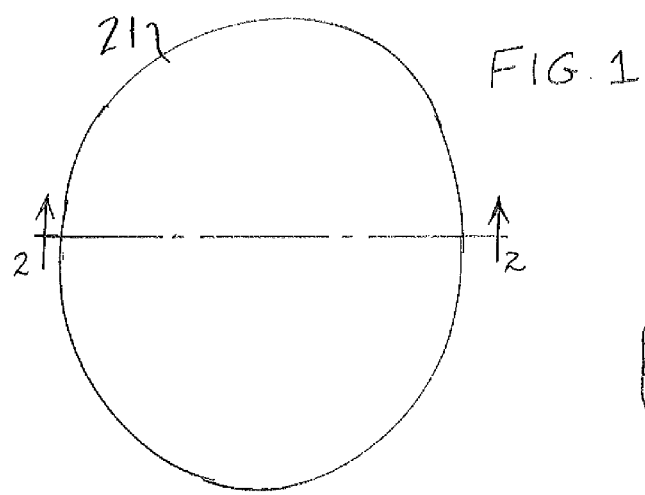
FIG. 1 is a schematic illustration of a sensor label fabricated and designed for single-use and disposability.
Figure 2:
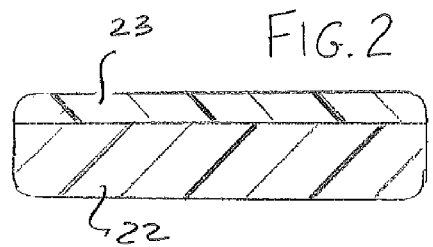
FIG. 2 is a schematic illustration of a cross-section along the line 2-2 of FIG. 1.

FIG. 1 illustrates a label of the type generally discussed herein, designated at 21. As seen in FIG. 2, this label can be a combination of a semi-permeable medium 22 having a parameter-sensitive and activatable developer 23. In an embodiment, the developer 23 is placed on the semi-permeable medium 22, typically in the form of a developer layer onto the medium which can be a single or multiple layers. A layer that supports the developer should be made of a semi-permeable material such a cellulosic member, for example a layer of paper. In embodiments, the parameter sensitive activatable developer 23 includes a solvent with a reactive chemical. When activated, the developer exhibits a detectable manifestation of a changed state that progresses over time. With such approaches, the disclosure relies on the progress of a solvent carrying a reactive chemical through a layer of the medium, such as a paper layer. FIG. 2 illustrates a single layered semi-permeable medium supporting the developer 23 that had been coated onto, printed on or impregnated into the medium 22.

The present disclosure finds particular application in providing sensor labels or tags that essentially rely on the progress of the solvent with reactive chemical being transformed to a developed or fixed state of the sensing layer. An embodiment of the label of FIG. 1 and FIG. 2 takes the form of an advanced temperature sensing label in which the developer 23 is a layer of a thermochromic ink placed on top of the semi-permeable medium 22. Such an ink includes a solvent carrying a chemical capable of developing or fixing the current state of the thermochromic in response to an environmental condition or conditions. When activated, the developer spreads along the semi-permeable medium at a defined rate, fixing the thermochromic ink, leaving a strip in which the color against length of the strip is a record of temperature against time. An optical reader then is employed It is noted the time scale is not necessarily linear inasmuch as the diffusion rate can also be a function of temperature, which can be compensated for mathematically. In this embodiment, reading of the detectable manifestation of the changed state of the thermochromic ink can be achieved by taking a color image of the label at this changed state of the label.

Apart from temperature-induced change, other parameters that can be recorded by operation of the label include shock. For example, a piezo electric layer such as fluoric polymers, including polarized polyvinylidene fluoride or polyvinylidene difluoride "(PVDF)", which provides a voltage that changes the alignment of a liquid crystal or drives charge into an electrochemical reaction. This reaction is fixed against time by the wave progressing with time through the permeable or semi-permeable layer. This can be considered a shock and time operational sensor label.

Another variation is a light sensor label, which can be important for articles that should not have been exposed to light when placed in a package except at specific times in transit from one place to another. For example, opening of the package containing the light sensor label will exhibit a detectable manifestation in the form of a changed state showing a compromise of security event had taken place. This can include an indication of when the compromise of security event occurred, such as by recording a level of detected light that reaches a threshold or benchmark. Thus, a light, radiation and time operational sensor label is provided.

A further variation is a chemical exposure sensor label. In an embodiment of this type, an article that is associated with a label developer in the nature of an enzyme or other sensor is sent through a shipping cycle, production process or other system where environmental exposure is possible and in need of sensing. Exposure to the chemical agent is recorded, as well as when the sensed-for event occurred. This allows the sensed-for (and usually detrimental) event to be located along the known transit path. A sensor alarm based event can be developed when a threshold magnitude, characteristic and/or location is reached.

Figure 3:
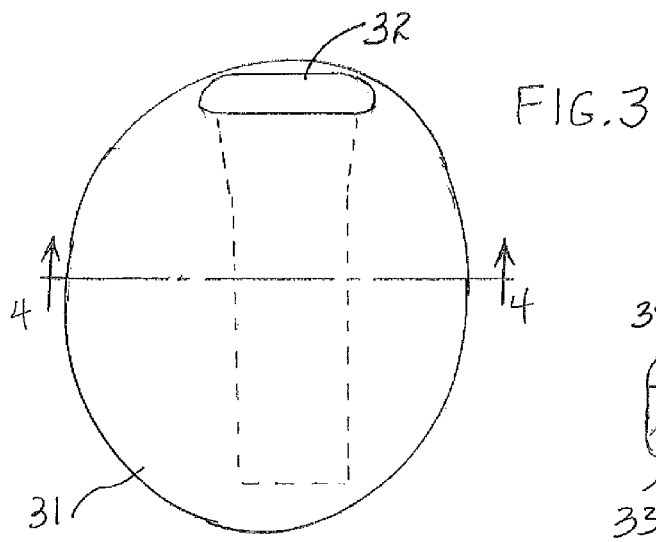
FIG. 3 is a schematic illustration of a sensor label fabricated and designed for single-time use and securement to an article of commerce, including an RFID component.
Figure 4:
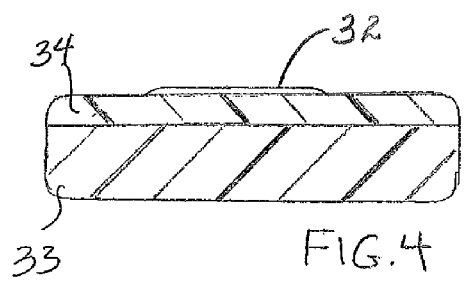
FIG. 4 is a schematic illustration of a cross-section along the line 4-4 of FIG. 3.

FIG. 3 and FIG. 4 illustrate a variation on the basic concept of FIG. 1. Here label 31 includes an RFID chip 32 which recognizes a detectable manifestation of change, and a recorder receives data from the RFID chip and logs parameter change data, typically against time. Often the recorder is remote from the RFID chip and thus of the sensor label and the article with which it is associated. Embodiments of this type can be useful in sensing parameters integrated with the RFID chip, which reads the sensor data against time electrically and then provides these data to a remote system of the type generally known for use in association with RFID transmission. Also shown is a support 33 and a sensor material 34.

Additional sensor labels are possible. These include sensor labels that follow activation methods wherein the pressure and temperature involved in thermal printing is employed to activate the sensing function of the sensor label and method. Various reagents exhibiting detectable manifestations of a changed state are available, including microencapsulated reagents.

Other embodiments, besides those illustrated herein, may also be employed without departing from the scope of the present disclosure. For example, the sensor label can be positioned on an article and/or within packaging of an article to detect tampering. Exposure of the sensor label and thus the article with which it is associated to acidic or caustic conditions that are damaging to the article can be addressed through the sensor label including the use of technology sensitive to pH changes. The method of the present disclosure can monitor viability of a material associated with the sensor label, such as monitoring articles for freshness and security maintenance, as well as addressing needs associated with risk management tracking, and to provide recordal of data and time profiles for archival, reporting and/ or quality control purposes.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A sensor label that is designed for and fabricated for single use or disposability that senses a parameter and records the sensed parameter, comprising:
   a semi-permeable medium;
   a parameter-sensitive and activatable developer on the semi-permeable medium, the developer, when activated exhibits a detectable manifestation of a changed state that progresses over time;
   the activatable developer is a piezo-electric that is configured to provide a voltage which changes in response to an environmental factor that is fixed against a time by a shock wave progressing during the time through the semi-permeable medium;
   a reader of the detectable manifestation of this changed state; and
   a recorder of the detectable manifestation of this changed state that logs parameter change data.

2. The sensor label in accordance with claim 1, wherein the reader notes time of the reading, and the recorder logs parameter change data against time.

3. The sensor label in accordance with claim 1, wherein the developer includes a reactive chemical within a solvent, and wherein the solvent carries the reactive chemical through a layer of the semi-permeable medium.

4. The sensor label in accordance with claim 1, wherein the semi-permeable includes a cellulosic layer or component.

5. The sensor label in accordance with claim 1, wherein the reader of the detectable manifestation is recognized by an RFID chip, and the recorder receives data from the RFID chip and logs the parameter change data against time.

6. The sensor label in accordance with claim 5, wherein the recorder is remote from the RFID chip.

7. The sensor label in accordance with claim 1, wherein the detectable manifestation is optically readable, the reader is an optical detector, and the recorder receives data from the optical detector and logs the parameter change data against time.

8. The sensor label in accordance with claim 1, wherein the changed state is a diffusion change of the developer with respect to the semi-permeable medium, and the detectable manifestation is with respect to the diffusion change.

9. The sensor label in accordance with claim 1, wherein the activatable developer is activated by an environmental factor selected from the group consisting of temperature, pressure, pH, moisture, shock, light, UV light, a gas, and combinations thereof.

10. The sensor label in accordance with claim 1, wherein the activatable developer is a light-sensitive component that changes in response to exposure to light beyond a threshold amount.

11. The sensor label in accordance with claim 1, wherein the activatable developer is an enzyme that changes in response to an environmental factor that is exposure to a chemical agent.

12. A method of using a sensor label for monitoring viability of a material associated with the label, comprising:

providing a sensor label that is designed for and fabricated for a single use or disposable including a semi-permeable medium having a parameter-sensitive and activatable developer that is selected from the group consisting of a piezo-electric layer, an enzyme layer, a micro-encapsulated reagent layer, and combinations thereof;

associating the label with a material to be monitored and positioning same into a given environment;

reading the detectable manifestation of this changed state; and recording the detectable manifestation of this changed state in order to log parameter change data against time.

13. The method in accordance with claim 12, wherein the reading notes time of reading and recording logs parameter change data against time.

14. The method in accordance with claim 12, wherein the reading employs an RFID chip and the recording cooperates with the RFID chip and logs parameter change against time.

15. The method in accordance with claim 12, wherein the reading employs an optical reader and the recording cooperates with the optical reader and logs parameter change against time.

16. The method in accordance with claim 12, further including activating the developer by an environmental factor selected from the group consisting of temperature, pressure, pH, moisture, shock, light, UV light, a gas, and combinations thereof.

* * * * *